US007910130B2

(12) United States Patent
Mohajer et al.

(10) Patent No.: US 7,910,130 B2
(45) Date of Patent: *Mar. 22, 2011

(54) STARCH DERIVATIVES AND OTHER DERIVATIVES, PRODUCTION PROCESSES THEREFOR, AND WOUND HEALING APPLICATIONS THEREFOR

(75) Inventors: Yousef Mohajer, Midlothian, VA (US); Irwin Kelman Cohen, Richmond, VA (US)

(73) Assignee: Tissue Technologies Holdings, LLC, Richmond, VA (US)

( * ) Notice: Subject to any disclaimer, the term of this patent is extended or adjusted under 35 U.S.C. 154(b) by 1227 days.

This patent is subject to a terminal disclaimer.

(21) Appl. No.: 11/289,646

(22) Filed: Nov. 30, 2005

(65) Prior Publication Data

US 2006/0142242 A1 Jun. 29, 2006

Related U.S. Application Data

(60) Provisional application No. 60/631,982, filed on Nov. 30, 2004.

(51) Int. Cl.
*A61L 15/16* (2006.01)
*A61L 15/00* (2006.01)
*A01N 43/04* (2006.01)
*A61K 31/70* (2006.01)

(52) U.S. Cl. .......... 424/446; 424/443; 424/445; 514/54; 514/495

(58) Field of Classification Search .................. None
See application file for complete search history.

(56) References Cited

U.S. PATENT DOCUMENTS

| | | | |
|---|---|---|---|
| 2,884,412 | A | 4/1959 | Neukom |
| 2,884,413 | A | 4/1959 | Kerr et al. |
| 2,993,041 | A | 7/1961 | Sietsema et al. |
| 3,238,100 | A | 3/1966 | Meyer et al. |
| 4,225,580 | A | 9/1980 | Rothman et al. |
| 4,537,767 | A | 8/1985 | Rothman et al. |
| 5,470,576 | A | 11/1995 | Patel |
| 6,015,816 | A | 1/2000 | Kostyniak |
| 6,156,334 | A | 12/2000 | Meyer-Ingold et al. |
| 6,306,419 | B1 * | 10/2001 | Vachon et al. ............ 424/422 |
| 6,599,523 | B2 * | 7/2003 | Cohen et al. ............ 424/443 |
| 6,627,785 | B1 | 9/2003 | Edwards et al. |
| 6,911,437 | B2 | 6/2005 | Edwards et al. |

FOREIGN PATENT DOCUMENTS

GB  2 221 620  2/1990

OTHER PUBLICATIONS

Thermoplastic and biodegradable polymers of cellulose, J. Simon, et al.; Polymer Degradation and Stability 59 (1998) 107-115.
Metal chelation of corn protein products/citric acid derivatives generated via reactive extrusion, D. Sessa, et al.; Industrial crops and Products; 10 (1999) 55-63.
Some studies on starch-urea-acid reaction mechanism, M. Khalil, et al.; National Research Center, Textile Division Dokki, Cairo, Egypt; Carbohydrate Polymers 48 (2002) 255-261.
Preparation of some starch-based neutral chelating agents, M. Khalil, et al.; National Research Center, Textile Division Dokki, Cairo, Egypt; Carbohydrate Research 324 (2000) 189-199.
Evaluation of nitrogen containing starch and hydrolyzed starch derivatives as a size base materials for cotton yarns, K. Mostafa; Textile Department, National Insitute for Standards; Carbohydrate Polymers 51 (2003) 63-68.
Thermogravimetric study of starch derivatives with amine/ammonium ion-exchanging groups in oxidative enviroment, I. Simkovic, et al.; Institute of Chemistry, Slovak Academy of Sciences, Carbohydrate Polymers 49 (2002) 509-513.
Physical stability and moisture sorption of aqueous chitosan-amylose starch films plasticized with polyols, M. Cervera, et al.; Insititute of Pharmacy and Food, University of Havana; European Journal of Pharmaceutics and Biopharmaceutics 58 (2004) 69-76.
Magnetic ion-exchange nano-and microparticles for medical, biochemical and molecular biological applications, C. Bergemann, et al.; Chemagen colloids, Bamberger Strasse, Journal of Magnetism and Magnetic Materials, 194 (1999) 45-52.
Starch derivatives of high degree of functionalization. 1. Effective, homogeneous synthesis of p-toluenesulfonyl (tosyl) starch with a new funtionalization pattern, T. Heinze, et al.; Institute of Organic Chemistry and Macromolecular Chemistry, Carbohydrate Polymers 42 (2000) 411-420.

* cited by examiner

*Primary Examiner* — Traviss C McIntosh, III
(74) *Attorney, Agent, or Firm* — Whitham Curtis Christofferson & Cook, PC (57) ABSTRACT

Novel phosphate starch derivatives are useful in wound healing. Novel phosphorylated cottons are useful in wound healing. Silver-derivatized wound care products are provided which survive washing and remain part of the wound care product. Silver-derivatized wound care products are provided that have favorable elastase-sequestering activity while advantageously appearing white-colored, without needing to darken to grey or black as usually would occur when working with silver. Also, starch products with outstanding water uptake are provided.

7 Claims, 3 Drawing Sheets

STARCH DERIVATIVES AND OTHER DERIVATIVES, PRODUCTION PROCESSES THEREFOR, AND WOUND HEALING APPLICATIONS THEREFOR

RELATED APPLICATION

This application claims benefit of U.S. provisional application No. 60/631,982 filed Nov. 30, 2004 titled "Starch derivatives for wound healing applications and process for their production."

FIELD OF THE INVENTION

This invention relates to treatment and care of wounds.

BACKGROUND OF THE INVENTION

Chronic Non-Healing Wounds: Clinically, wounds are categorized as acute or chronic based on the timeliness of healing. The normal response to tissue injury is a timely and orderly reparative process that results in sustained restoration of anatomic and functional integrity. In contrast, in chronic ulcers, the healing process is prolonged, incomplete, and proceeds in a disorganized manner resulting in poor anatomical and functional outcome. Most chronic ulcers are associated with a small number of well-defined clinical diseases particularly chronic venous hypertension, diabetes mellitus, and pressure ulcers. These conditions are responsible collectively for approximately 70% of all chronic ulcers. The incidence of chronic ulcers continues to increase because of such factors as increased longevity and the logarithmic increase in the incidence of Type II Diabetes throughout the world. In addition to these non-healing skin wounds, there are many other conditions characterized by excessive protease activity and disease chronicity, for example, oral inflammatory diseases such as gingivitis.

Pressure ulcers are an example of a chronic wound. They are characterized by deep tissue necrosis with loss of muscle and fat that is disproportionately greater than the loss of overlying skin. The incidence and prevalence of chronic pressure ulcers vary considerably but are especially high in spinal cord injury patients as well as the elderly and nursing home populations. Health care expenditures for treating pressure ulcers alone had been estimated to exceed $3 billion a year. Wound care is a significant part of the cost. Moreover, the incidence of pressure ulcers increases yearly worldwide because of increased longevity and trauma. There is similar data for diabetic wounds. The number of these wounds is increasing substantially because of an aging population, obesity and subsequent increased incidence of type II diabetes throughout the world.

Proteolytic Environment of Chronic Wounds: Normal healing involves a complex cascade of events involving interaction among many cell types, soluble factors and matrix components. Healing can be divided arbitrarily into overlapping temporal phases of coagulation, inflammation, fibroplasia, and finally remodeling. Cytokines (growth factors) are universally believed to be essential regulators for the repair process. Therefore, destruction of cytokines by proteases may retard healing. Normally, during the inflammatory phase, polymorphonuclear leukocytes (PMNs) are the first of the leukocytes to appear. They produce various proteases such as collagenase (MMP-8) and elastase, which help to remove damaged matrix and aid in healing. In both the acute and the chronic wounds, various cytokines are important in angiogenesis, contraction, collagen synthesis/degradation and subsequent wound closure. Under normal circumstances, closure of the open wound is aided further by epithelial (keratinocyte) cells which seal the wound for final closure. The healing of the chronic wounds is very different than normal healing. The same proteases which are part of the normal healing process become excessive because of the continued high levels of PMNs. These proteases then destroy matrix, growth factors and growth factor receptor sites. The pressure sore will be used for illustration of the chronic wound.

Neutrophils are the predominant infiltrating inflammatory cell type present in the acute inflammatory response. Neutrophils function primarily to destroy invading pathogens and to debride devitalized tissue at the site of injury. The normal adult produces approximately $10^{11}$ neutrophils per day. To function effectively in host defense, they must migrate to the site of inflammation and release selectively a large repertoire of proteolytic enzymes, antimicrobial peptides and potent oxidants from cytoplasmic granules. Under other conditions, the neutrophil has been implicated in causing disease by damaging normal host tissue. Such inflammatory tissue injury is important in the pathogenesis of a variety of clinical disorders including arthritis, ischemia-reperfusion tissue injury and systemic inflammatory response syndrome (SIRS) and the acute respiratory distress syndrome (ARDS). There is strong evidence that neutrophils also may have a significant role in the pathophysiology of chronic wounds.

Neutrophils are a prevalent cell type in pressure ulcers and other chronic wounds. In addition, there is direct evidence correlating neutrophil products with chronic pressure ulcers. Therefore, these observations have led to the hypothesis that neutrophil products are involved significantly in the pathogenesis of pressure sores and their subsequent failure to heal.

Neutrophils contain large amounts of elastase (1 pg/(cell). This serine protease is elevated significantly in fluid derived from pressure ulcers and other chronic wounds. The presence of high levels of active elastase within a wound site has important implications for ulcer pathogenesis and subsequent failure to heal. For example, elastase present in chronic wounds can degrade peptide growth factors such as PDGF and TGF-β. Moreover, cell surface receptors for peptide growth factors may themselves be functionally inactivated by the actions of elastase. Therefore, treatment of chronic wounds with growth factors is ineffective in the presence of high levels of elastase. Clinically, platelet derived growth factor (PDGF) fails to effectively promote healing of pressure sores because these wounds contain high levels of elastase (which destroys PDGF). In addition, elastase is known to proteolytically inactivate the specific inhibitor Tissue Inhibitor of Metalloproteinases (TIMP). Therefore, collagenase activity may actually become greater to further retard healing. In addition, elastase itself may participate in proteolytically activating collagenase and gelatinase zymogens.

Chronic wound treatments: Over the past two decades, many manufacturers have marketed "advanced wound care products" for the management of various chronic wounds. These include hydrocolloids, hydrogels and calcium alginates. However, there is little evidence that the rate of healing or cell biology of the wound has been altered by these products. In fact, in wet wounds, it is quite appropriate to use a dressing that is dry when placed in the wound.

There has been some activity in the patent literature thus far disclosing some approaches relating to wounds, as evidenced by the following.

U.S. Pat. No. 3,238,100 (issued Mar. 1, 1966) by Meyer et al., titled "Starch phosphate film composition and method of dressing wounds with same" discloses utility of a phosphorylated starch in wound healing. He reported that phosphorylated starches could be blended with regular starch, gelatin, pectin or carboxymethylcellulose to form strong transparent films. Apparently in the absence of phosphorylated starch, one cannot get clear strong films from starch and gelatin due to the lack of compatibility. Meyer described making a transparent film by dissolving a conventional phosphorylated starch in water with and without gelatin and casting 3-mil films. After sterilization, he compared healing performance of his clear film dressings against conventional gauze containing petroleum gel on burn wounds in dogs. Meyer described films prepared from the phosphorylated starches and their utility in wound healing. Meyer et al. also refer to the starch phosphate derivatives of U.S. Pat. Nos. 2,884,412; 2,884,413 and 2,993,041.

U.S. Pat. No. 4,225,580 (issued Sep. 30, 1980) and U.S. Pat. No. 4,537,767 (issued Aug. 27, 1985) both by Rothman et al., titled "Method for cleansing fluid discharging skin surfaces, wounds and mucous membranes and means for carrying out the method."

U.S. Pat. No. 6,156,334 (issued Dec. 5, 2000) by Meyer-Ingold et al., titled "Wound coverings for removal of interfering factors from wound fluid."

U.S. Pat. No. 6,306,419 (issued Oct. 23, 2001) by Vachon et al. (Aegis Biosciences, LLC), titled "Medical uses of styrene sulfonate polymers" discloses use of silver as a therapeutic agent for wound dressings. They teach use of silver to impart antimicrobial activity to coated fabrics. They describe that when a fabric is coated with a styrene sulfonate polymer and then equilibrated with soluble silver solution until silver is partially reduced to metallic silver, the fabric becomes antimicrobial.

U.S. Pat. No. 6,599,523 (issued Jul. 29, 2003) by Cohen et al., titled "Preparation of peroxide-oxidized, sulfonated, and phosphorylated cotton."

U.S. Pat. No. 6,627,785 (issued Sep. 30, 2003) by Edwards et al., titled "Wound dressings with protease-lowering activity."

U.S. Pat. No. 6,911,437 (issued Jun. 28, 2005) by Edwards et al., titled "Saccharide derivatives especially useful in wound dressings."

However, the present inventors have considered the state of the art and find that there still remain needs for better materials to promote wound healing for various kinds of wounds. For example, conventional wound dressings generally suffer from one or more of the problems of not swelling much to absorb fluid, little or no elastase and collagenese sequestering and/or loss of silver content (if any) upon a first washing.

SUMMARY OF THE INVENTION

The above problems and shortcomings relating to wound healing have been addressed by the present invention. A variety of starch derivatives and cotton materials, respectively, have been provided.

New starch-based materials have been invented, especially for wound healing applications. The present inventors have discovered new derivatives of starches (such as, e.g., phosphorylated starches, silver derivatived starches, urea derivative starches, and combinations thereof, with phosphorylated urea starches being preferred) which selectively sequester elastase and collagenase from a wound are effective in various wound healing applications. Starch is an abundant low-cost natural material with potential for many chemical modifications by various facile reactions. Additionally, starch-based materials can be formed into many useful forms for wound healing applications.

New silver-derivatized materials also have been invented, such as, e.g., silver derivatized starches and silver derivatized cottons, etc. By derivatizing the silver into the compound, the silver advantageously remains with the compound and thus, when formulated into a wound dressing product, survives washing activity and is released slowly.

Using the present invention, wound dressing products may be formulated wherein patient wound care may be improved with regard to one or more of fluid absorption through better swelling of a wound dressing, better elastase and collagenese sequestering activity and/or better retention of silver content surviving a first washing and is slow released for antimicrobial activity. For example, inventive starch products with exceptional water uptake capacity are provided.

In a preferred embodiment, the invention provides a starch derivative comprising a starch-derived compound containing a urea network, wherein the compound when exposed to water swells, at room temperature, at least 10 times dry weight (preferably, a starch derivative wherein the swelling is at least 20, more preferably at least 30, times dry weight), such as, e.g., a starch derivative wherein the starch-derived compound is phosphorylated; a starch derivative wherein the starch-derived compound has a sequestering activity for elastase of 45% or greater (preferably, a sequestering activity for elastase of 55% or greater); a starch derivative wherein the starch-derived compound has a sequestering activity for collagenase of 50% or greater (preferably, a sequestering activity for collagenase of 70% or greater); etc.

In another preferred embodiment, the invention provides a starch derivative having the following formula (I):

wherein: "St" means a subunit of starch; k+l+m+p=3; k is equal or less than 0.5; l, m, and p are numbers between zero and 3 inclusive and may be fractions; "Z" is selected from the group consisting of: C(O)NH$_2$; C(S) NH$_2$; C(O)NH$_3$.A or C(S)NH$_3$.A wherein "A" is selected from the group consisting of an anion of phosphoric acid, sulfuric acid, nitric acid, hydrochloric acid and perchloric acid); C(O)-St; and C(S)-St; and W comprises a condensation product CH$_2$R wherein R is selected from the group consisting of: —NH—C(O)—NH$_2$; —NH—C(O)—NH—CH$_2$—OSt; —NH—C(S)—NH$_2$; —NH—C(S)—NH—CH$_2$—OSt; a melamine group; a melamine group wherein an NH$_2$ group is attached to CH$_2$—OSt; any combination thereof and any chain extended version thereof and wherein W may be substituted or unsubstituted; and wherein negative charge on the PO$_3^-$ is neutralized by a cation (e.g., Na$^+$, K$^+$, H$^+$, Li$^+$), such as, e.g., a starch derivative wherein W is a thiourea formaldehyde condensation product; a starch derivative comprising derivatized silver, wherein the silver is complexed to the starch; etc.

In another preferred embodiment, the invention provides a cotton derivative compound comprising a cotton and at least one selected from the group consisting of: a urea derivative; a thiourea derivative; a condensation product of urea and formaldehyde; a condensation product of thiourea and formaldehyde; and, a condensation product of melamine and formaldehyde, such as, e.g., a cotton derivative compound comprising thiourea and cotton; a cotton derivative compound comprising a condensation product of thiourea and formaldehyde; a cotton derivative compound wherein the cotton derivative is phosphorylated; a cotton derivative compound including complexed silver; etc.

In another preferred embodiment, the invention provides a wound treatment product, comprising at least one of: (A) a starch derivative containing a urea network, wherein the starch derivative when exposed to water swells, at room temperature, at least 10 times dry weight; (B) a starch derivative having formula (I); or (C) a cotton derivative compound comprising a cotton and at least one selected from the group consisting of: a urea derivative; a thiourea derivative; a condensation product of urea and formaldehyde; a condensation product of thiourea and formaldehyde; and, a condensation product of melamine and formaldehyde. Preferred examples of inventive wound treatment products are, e.g., a wound treatment product including a starch derivative that is phosphorylated; a wound treatment product including a starch derivative containing a urea network, wherein the starch derivative when exposed to water swells, at room temperature, at least 10 times dry weight; a wound treatment product including a starch derivative according to formula (I); a wound treatment product including a urea derivative and/or a thiourea derivative; a wound treatment product further including silver; etc.

The invention in another preferred embodiment provides a process for producing a phosphate starch derivative, comprising at least the step of: (a) mixing a starch with a phosphorylating reagent in presence of a conjugating reagent (such as, e.g., a conjugating reagent selected from the group consisting of a urea compound; a thiourea compound; biuret; melamine; cyanuric acid; a urea formaldehyde condensation product; and a thiourea formaldehyde condensation product), such as, e.g., a process wherein a starch derivative of formula (I) is formed. Optionally the process for producing a phosphate starch may further include a step (b) of derivatizing the starch with a silver compound (such as a silver compound selected from the group consisting of silver nitrate, silver acetate, silver perchlorate, silver fluoride and silver chlorate), wherein the process produces a silver-containing phosphate starch derivative.

BRIEF SUMMARY OF THE DRAWINGS

FIGS. 1A, 1B are dry samples. FIG. 1C is FIG. 1A after wetting with water; FIG. 1D is FIG. 1B after wetting with water. The phosphorylated starch of FIG. 1B corresponds to inventive Example 3 herein. FIG. 1A is a conventional phosphorylated starch.

DETAILED DESCRIPTION OF A PREFERRED EMBODIMENT OF THE INVENTION

In a preferred embodiment of the invention, inventive materials, products, wound dressings, gum molds, etc. of the present invention may be produced from starch (see FIG. 5) which in its native (underivatized) form is made up of two types of molecules, amylose and amylopectin. Amylose is a linear (1,4)-alpha-D-glucan. Amylopectin is a branched macromolecule containing both (1,4)alpha-D linkage and (1,6) alpha-D connections at the point of branching. While the degree of polymerization is between 350-1000 for amylose, the value for amylopectin is many times greater (very large branched macromolecules). Because of the amylopectin content, starch is a very open structure lending itself to many derivatization reactions. Regular, basic starch may be written as the following chemical formula: $[-St-(OH)3]_n$ where "St" is $C_6H_4O_2$ and "n" is between 100 and 10,000 (inclusive).

Figure 5:
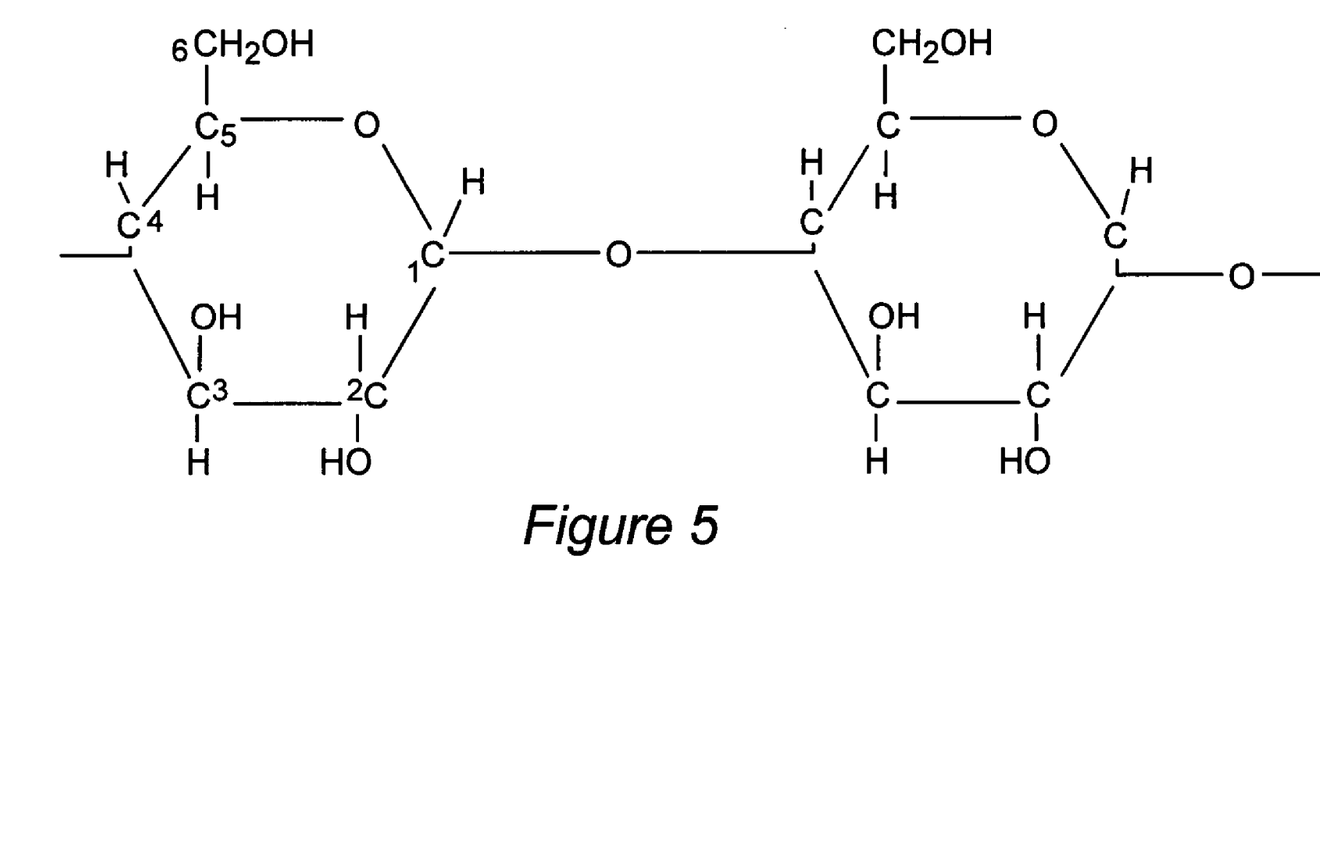
FIG. 5 is a chemical formula of a basic repeating unit of starch. Starch is composed of about 25% amylose (anhydroglucopyranose units joined by glucosidic bonds) and 75% amylopectin, a branched-chain structure. Starch occurs in plants such as corn, potatoes, tapioca, rice, and wheat.

The term "derivative" is used herein to mean a compound which is produced or may be produced by one or more chemical reactions from the identified base compound, which is believed to be in accord with its usage in the patent and technical literature. For example, a "starch derivative" means a compound which is produced, or may be produced, by one or more chemical reactions from starch (FIG. 5).

Before the present invention, many interesting starch derivatives have been known and have had food, cosmetic and other industrial applications. For example, hydroxyl functionalities in starch can be etherified forming starch esters with varying range of solubilities and film forming properties. Ester and ether derivatives of starches are used in papermaking, textile and coating industries. Cationic starches are prepared from reaction of the hydroxyl on the starch with various reagents forming starches with positive charges and greater range of solubilities. These very soluble starches have uses in paper, textile and coating applications. Anionic starches have been reported from phosphorylation of starches by forming phosphate esters. These negatively charged starches have been reported to be compatible with gelatin, poly(vinyl alcohol) and polyacrylates.

There is technical literature regarding starch chemistry and starch derivatives. See, e.g., M. I. Khalil et al., "Preparation of some starch-based neutral chelating agents," Carbohydrate Research 324 (2000), 189-199; M. I. Khalil et al., "Some studies on starch—urea—acid reaction mechanism," Carbohydrate Polymers 48 (2002) 255-261; Kh. M. Mostafa, "Evaluation of nitrogen containing starch and hydrolyzed starch derivatives as a size base materials for cotton yarns," Carbohydrate Polymers 51 (2003) 63-68; K. Simkovic et al., "Thermogravimetric study of starch derivatives with amine/ammonium ion-exchanging groups in oxidative environment," Carbohydrate Polymers 49 (2002) 509-513; M. F. Cervera, et al., "Physical stability and moisture sorption of aqueous chitosan—amylose starch films plasticized with polyols," European Journal of Pharmaceutics and Biopharmaceuetics 58 (2004) 69-76; Magnetic ion-exchange nano- and microparticles for medical, biochemical and molecular biological applications," Journal of Magnetism and Magnetic Materials 194 (1999) 45-52; T. Heinze et al., "Starch derivatives of high degree of functionalization. 1. Effective, homogeneous synthesis of p-toluenesulfonyl (tosyl) starch with a new functionalization pattern," Carbohydrate Polymers 42 (2000) 411-420.

One kind of starch derivative is phosphorylated starch. Certain phosphorylations of starch have been known and practiced for over seventy years. U.S. Pat. No. 2,884,413 to Kerr et al gives details of preparation of mono and cross-linked starch phosphates using a variety of inorganic phosphates including sodium metaphosphate, polyphosphate, hexametaphosphate, and pyrophosphate. The previously-reported phosphorylated starches have had interesting properties for food and industrial applications. Depending on the reaction conditions such as the concentration of the reagents, reaction time, pH, temperature and the concentration of water, products can be formed with very low degree of phosphorylation (Starch, James Daniel et al., Volume 33 of Ullmann's Encyclopedia of Industrial Chemistry, Wiley-VCH 2003, pp 721-745).

The present invention provides novel phosphorylated starches of the following formula (I):

$$[-St-(OPO_3^-H)_k(OH)_l(O-Z)_m(O-W)_p]  \quad (I)$$

wherein: "St" means a subunit of starch; k+l+m+p=3; k is equal or less than 0.5; l, m, and p are numbers between zero and 3 inclusive and may be fractions; "Z" is selected from the group consisting of: $C(O)NH_2$; $C(S)NH_2$; $C(O)NH_3.A$ or $C(S)NH_3.A$ wherein "A" is selected from the group consisting of an anion of phosphoric acid, sulfuric acid, nitric acid, hydrochloric acid and perchloric acid); C(O)-St; and C(S)-St; and W comprises a condensation product $CH_2R$ wherein R is selected from the group consisting of: —NH—C(O)—$NH_2$; —NH—C(O)—NH—$CH_2$—OSt; —NH—C(S)—$NH_2$; —NH—C(S)—NH—$CH_2$—OSt; a melamine group; a melamine group wherein an $NH_2$ group is attached to $CH_2$—OSt; any combination thereof and any chain extended version thereof and wherein W may be substituted or unsubstituted; and wherein negative charge on the $P_3O^-$ is neutralized by a cation (e.g., $Na^+$, $K^+$, $H^+$, $Li^+$), such as, e.g., a starch derivative wherein W is a thiourea formaldehyde condensation product; a starch derivative comprising derivatized silver, wherein the silver is complexed to the starch; etc. Thiourea products are preferred for use in the phosphorylated starches of formula (I).

A conventional reaction of starch with monosodium phosphate (MSP) produces starch with a negative charge but does not generate phosphorylated starches according to formula (I). Phosphorylated starches according to formula (I) may be made by reaction of a starch with a phosphorylation reagent along with at least one conjugating reagent.

Examples of a starch useable in the invention are, e.g., corn starch, potato starch, pea starch, tapioca starch, rice starch, wheat starch, jackbean starch, breadfruit starch, sorghum starch, sago starch, etc., as non-limiting examples.

"Phophorylation reagent" as used herein refers to any compound capable of phosphorylating a starch or a cotton. Examples of a phosphorylation reagent useable in the invention are, e.g., a phosphorylation reagent solution comprising ammonium dihydrogen phosphate; monosodium phosphate (MSP); sodium metaphosphate (SMP) $(Na_6(PO_3)_6)$; monoammonium phosphate (MAP) $(NH_4H_2PO_4)$ (also referred to as ammonium dihydrogen phosphate); diammonium phosphate (DAP) $(NH_4)_2H\ PO_4$ (also referred to as ammonium phosphate); other ammonium phosphates; monobasic phosphorylating reagents (e.g., MAP, etc.); dibasic phosphorylating reagents (e.g., DAP, etc.); sodium, potassium, and lithium orthophosphates and any combination thereof (see, e.g., U.S. Pat. No. 2,993,041); tripolyphosphate (see, e.g., U.S. Pat. No. 2,884,413); alkali metal phosphate salt or combination of salts (see, e.g., U.S. Pat. No. 2,884, 412); sodium metaphosphate, sodium tripolyphosphate, sodium hexametaphosphate, tetrasodium pyrophosphate (see, e.g., U.S. Pat. No. 2,884,418); other phosphorylating reagents; etc. The mentioned phosphorylation reagents are non-limiting examples. Combinations of phosphorylating reagents may be used, such as, e.g., phosphoric acid in combination with any phosphate pyrophosphate, orthophosphate and/or neutralizing agents to provide pH in a range of 1.5 to 10.0 (preferably in a range of 3.0 to 9.0). Lower pH is avoided because phosphoric acid in low pH causes caramelization and carbonization of cotton and starch at a curing temperature of about 130 to 160 C. A phosphorylating reagent may be used in mixture with a conjugating reagent (such as urea, etc.) in any proportions.

Examples of a conjugating reagent useable in the invention are, e.g., urea, thiourea, biuret, cyanuric acid, urea formaldehyde, melamine, and other active nitrogen-containing compounds. Using urea for derivatizing starch is particularly preferred.

The ratio of conjugating reagent to phosphorylating reagent may be in a range of about 10:1 to 1:2, with a ratio of about 3:1 being preferred. The ratio of starch to solution may be in a range of about 0.1:10 to 1:1, with about 2:5 being a preferred example. The ratio of starch to phosphorylating reagent, and the ratio of starch to conjugating ratio depend on the solution composition. It is preferred to begin with determining ratio of conjugating reagent to phosphorylating reagent and thereafter determine other reagents.

For mixing the conjugating reagent, phosphorylating reagent and the starch, a temperature range is about 10 to 30 C (preferably 20-25 C), such as, e.g., mixing at room temperature, preferably for a short duration such as about 1 to 10 minutes, most preferably in a range of about 2 to 3 minutes. For the post-mixing spreading and drying of the material, and thereafter for the curing, the conditions depend on the quantity of material. For a quantity of material of about 2 to 5 grams, post-mixing spreading and drying may be conducted at a temperature in a range of about 70 to 95 C (preferably 80-90 C) for about 10 to 30 minutes (preferably for about 10 to 15 minutes). Subsequent curing preferably is conducted at a temperature in a range of about 130-170 C (preferably about 150-160 C), for a time of about 3 to 15 minutes (preferably for about 6 to 10 minutes).

For example, in the invention there may be used a solution made by dissolving solid urea and ammonium dihydrogen phosphate (such as, e.g., monoammonium phosphate, MAP) and deionized water (such as, e.g., deionized water containing Triton X-100 SigmaUltra). As another example, a phosphorylation reagent, conjugating reagent and starch may be mixed into a solution or slurry, which may be cast onto a surface (preferably being spread uniformly) and then dried (such as, e.g., oven-dried at a temperature in a range of about 85-95 C for a time of about 30 minutes), followed by curing (such as, e.g., cured at about 160 C for about 6 minutes, preferably in a press oven), cooling, and peeling from the surface a formed film which may be used as is, or further processed (such as, e.g., processing into a fine powder). An example of processing the film into a powder is, e.g., to place the film in a liquid (such as deionized water), allowing swelling and then settling to occur, followed by washing (such as with deionized water), filtering, and drying (such as, e.g., drying at room temperature), wherein a fine powder results.

Inventive phosphorylated starch derivatives prepared using a phosphorylating agent, a starch and a conjugating reagent may be used in that form, or, optionally, but preferably, phosphorylated starches may be further processed, such as, e.g., conversion into their silver salts (such as, e.g., by treating a phosphorylated starch with a soluble silver (such as, e.g., silver nitrate, silver acetate, silver perchlorate, silver fluoride, silver chlorate, etc.). Inventive silver phosphorylated starch derivatives are thereby produced. Soluble silver compounds used in the invention may be soluble in, e.g., water, alcohol (such as methanol, ethanol, propanol, ethylene glycol, glyme), etc.

The novel phosphate starch derivatives are especially useful for formulation into wound dressings. For example, starch derivatives in the form of a film may be placed onto a wound in need of treatment. As another example, starch derivatives in powder form may be sprinkled onto or into a wound in need of treatment. Also, starch derivatives may be formed into other wound dressing products. The starch derivatives of the invention can be used in various forms of wound dressings (such as, e.g., powder, sprays, liquids, gels, sheets, films, gauzes, etc.); incorporated into hydrocolloids, hydrogels, algenates, cotton, sprays, atomizers, etc.; incorporated into solutions which may be molded around gums for treatment of gingivitis and used for periodontitis and dressings after intraoral surgery applications; etc. Slurries formulated using starch derivatives according to the invention may be introduced orally or by enema, for example for treatment of ulcerative colitis. Dressings or bandages of the invention may be appropriate for enterostomal care including colonostomy, iliostomy, and uretorostomy, and for vasculitis secondary to connective tissue disease. Chronic wounds including pressure sores, diabetic ulcers, venous stasis ulcers, and connective tissue disease ulcers, and burn wounds can be effectively treated by wound dressings of the invention. These forms are mentioned as examples of uses of the starch derivatives and are not limiting.

In the case of treating gingivitis, the inventive starch derivatives are particularly suited because a popular therapy for gingivitis is low dose Doxycycline, a tetracycline which is a known inhibitor of MMP-8. Molding the inventive starch derivatives which are protease inhibitors in an appropriate material may be used to provide a therapeutic material around the gums as adjuvant therapy for gingivitis. Additionally, protease inhibitors may be provided in an appropriate material to mold around the gums as a dressing after periodontal surgery.

A powder form of starch derivatives may be generated, e.g, by coating starch with an aqueous solution containing the phosphorylating agent such as sodium dihydrogen phosphate and the conjugation reagent. After drying at 60 C to remove water, the coated starch is heated in oven for 1 to 15 minutes at appropriate temperature. The temperature is between 100 to 160 C and depends on the nature of the phosphorylation reagent. After reaction, the product is suspended and washed in water and separated by filtrations then it is dried at a temperature range of 60-95 C. The powder may be used as such, or may be enclosed in a casing to allow permeation of wound fluids to the powder form while restraining direct contact of the powder with tissue. Various forms of semipermeable materials are available including those made form cellulose and polyvinyl alcohol.

A film form of starch derivatives may be made, e.g., by mixing starch with an aqueous solution of phosphorylating reagents. It is then heated gently to form a viscous solution which will be knife-coated on a release film (such as, e.g., Reynolds Wrap commercial aluminum foil coated with silicon release film). The aluminum foil containing the starch film in the form of viscous solution is then heated at 60-90 C to remove water. Then another aluminum release foil is placed on top and then cured at 130-170 C. After removing the release film a semitransparent film is obtained.

A fabric form may be produced by coating cotton gauze with aqueous phosphorylating solutions containing starch. After drying at 60-90 C to remove water the coated gauze is heat treated at a temperature of 140-170 for 1 to 15 minutes. The product is then rinsed with water and dried.

A gel form may be produced by permitting a starch derivative powder to take up aqueous solution, forming a gel. Optionally the aqueous solution may include other ingredients such as gelatin, glycerin, polyvinyl alcohol and antimicrobials.

A moldable form may be produced by coating starch with phosphorylating reagent containing the conjugate reagent. After drying to remove water, the product is collected as a powder, which can be compression molded to desired form. Optionally other polymers can be included to obtain desire physical properties.

An inventive starch derivative which passes safety screening may be used directly in a patient. An inventive starch derivative which has not been so screened may be prepared for clinical use by placement within a hydrocolloid or hydrogel, to isolate the starch derivative from the patient and thus avoid any question of soft tissue reaction (as may be observed when applying native starch). Additionally, the hydrocolloid or hydrogel form may be more generally used, for safety-screened and unscreened starch derivatives, to provide desired designs of hydrophilic and hydrophobic dressings which can be selected depending on the nature of a patient's particular wound.

Above there have been mentioned optional silver derivatives and optionally incorporating silver into wound care products. In addition to certain improved elastase-sequestering advantages which may be imparted in certain embodiments of cotton products by silver-derivatizing a cotton product, the present inventors further now provide certain cotton silver derivatives which, unlike conventional silver derivatives, do not need to convert ionic silver to metallic silver (grey to black color). Thus, the present invention provides certain cotton wound care products that are effective for wound treatment even when the cotton product is white in color. Thus, the present invention provides the ability in certain embodiments to control the color of a cotton wound care product to a desirable white color, or alternately to other desired colors such as a bright colored antimicrobial product. Such colored-controlled (such as, e.g., white-colored) silver derivative cotton wound care products are prepared according to the above-mentioned silver derivatizing of cotton, with particular avoidance of contact with intensive ultraviolet light such as sun or extended exposure to fluorescent light (which could convert the product to a grey or black color). Preferably, silver is derivitized in minimal light and a resultant cotton product (such as a fabric-based product) is dried to form a white-colored cotton product. Preferably the dried cotton product (such as a dried white-colored silver-derivitized product) is stored away from direct ultraviolet light.

The invention may be appreciated with regard to the following Examples, without the invention being limited to those Examples.

In the examples that follow, corn starch (Argo 100% food grade) has been used, but the invention is not limited to corn starch. Other starches such as those obtained from natural sources such as potato, wheat, yam, and peas could also be used.

Inventive Example 1

Starches

A solution of phosphorylation reagent was made by dissolving 3.00 grams of solid urea (99.5% from Across, Catalog Number 140750010) and 1.00 grams of ammonium dihydrogen phosphate (monoammonium phosphate, MAP), (Across, Reagent grade, Catalog Number 423385000) and 6 ml of deionized water containing Triton X-100 SigmaUltra (Sigma T9284) at 0.1% by weight. The solution was mixed for 10 minutes at 3540 C, and then 1.3 grams of corn starch was added to the solution and mixed with good agitation at 35-40 C for additional 15 minutes. The high viscosity solution/ slurry was then cast on Reynolds Wrap Release Non-Stick Aluminum Foil. A blade was used to spread the materials uniformly and then dried on an oven at 85-95 C for 30 minutes. The sample was then cured at 160 C for 6 minutes by placing in a press oven. The press oven ensures immediate transfer of heat from oven to samples. After removing and cooling, the sample was peeled from the release aluminum sheet. The resulting product was in the form of a semitransparent film. (It could be used as is.) In this Example, we placed the product in 400 ml of deionized water and allowed it to swell into the slurry which was allowed to settle; then it was washed with two additional 400 ml of deionized water and filtered and dried at room temperature to a fine powder. Alternately Teflon coated aluminum film instead of Reynolds Wrap can be used with equal result.

Comparative Example 1

Phosphorylation of the starch was carried out in the exact manner as Inventive Example 1 above with the exception that the conjugating reagent, urea, was absent. A solution of phosphorylation reagent was made by dissolving 1.00 grams of ammonium dihydrogen phosphate (monoammoniumphosphate MAP) (Across, Reagent grade, Catalog Number 423385000) and 6 ml of deionized water containing Triton X-100 SigmaUltra (Sigma T9284) at 0.1% by weight. The solution was mixed for 10 min at 35-40 C, and then 1.3 grams of corn starch, Argo 100% food grade, was added to the solution and mixed with good agitation at 35-40 C for additional 15 min. We did not observe any viscosity built up during this step. The slurry was then cast on Reynolds Wrap Release Non-Stick Aluminum Foil. A blade was used to spread the materials uniformly and then dried on an oven at 85-95 C for 30 min. The sample was then further reacted at 160 C for 6 minutes by placing in oven. After cooling, the sample was removed from the release aluminum sheet. The resulting product was in the form of a powder. We placed the product in 400 ml of deionized water and mixed and then it was allowed to settle; then it was washed with two additional 400 ml of deionized water and filtered and dried at room temperature to a fine powder.

Inventive Example 2

Diammoniumhydrogenphosphate (DAP) was used as the phosphorylation reagent, along with urea. A solution of phosphorylation reagent was made by dissolving 3.00 grams of solid urea (99.5% from Across, Catalog Number 140750010) and 1.00 grams of DAP (Across, Reagent grade, Catalog Number 201825000) and 6 ml of deionized water containing Triton X-100 SigmaUltra (Sigma T9284) at 0.1% by weight. The solution was mixed for 10 minutes at 35-40 C, and then 1.3 grams of corn starch, Argo 100% food grade, was added to the solution and mixed with good agitation at 35-40 C for additional 15 minutes. The high viscosity solution/slurry was then cast on Reynolds Wrap Release Non-Stick Aluminum Foil. A blade was used to spread the materials uniformly and then dried on an oven at 85-95 C for 30 minutes. The sample was then cured at 160 C for 6 minutes in press oven. After removing and cooling, the sample was peeled off from the release aluminum sheet. The resulting product was in the form of a semitransparent film. (It could be used as is.) The product was placed in 400 ml of deionized water and allowed to swell into the slurry which was allowed to settle; then it was washed with two additional 400 ml of deionized water and filtered and dried at room temperature to a fine powder. (Teflon coated aluminum film may be used instead of Reynolds Wrap with equal result.)

Comparative Example 2

Phosphorylation of the starch was carried out in the same exact manner as inventive Example 2 above with the exception that the conjugating reagent, urea, was absent. A solution of phosphorylation reagent was made by dissolving 1.00 grams of DAP (Across, Reagent grade, Catalog Number 201825000) and 6 ml of deionized water containing Triton X-100 SigmaUltra (Sigma T9284) at 0.1% by weight. The solution was mixed for 10 minutes at 35-40 C, and then 1.3 grams of corn starch, Argo 100% food grade, was added to the solution and mixed with good agitation at 35-40 C for additional 15 minutes. We did not observe any viscosity built up during this step. The slurry was then cast on Reynolds Wrap Release Non-Stick Aluminum Foil. A blade was used to spread the materials uniformly and then dried on an oven at 85-95 C for 30 minutes. The sample was then further reacted at 160 C for 6 minutes by placing in oven. After cooling, the sample was removed from the release aluminum sheet. The resulting product was in the form of a powder. We placed the product in 400 ml of deionized water and mixed and then it was allowed to settle; then it was washed with two additional 400 ml of deionized water and filtered and dried at room temperature to a fine powder.

Inventive Example 3

In this example the phosphorylation agent sodium meta phosphate (SMP), (sodium hexametaphosphate, Across catalog Number 61217-5000) and the conjugating reagent urea were used. A solution of phosphorylation reagent was made by dissolving 3.00 grams of solid urea (99.5% from Across, Catalog Number 140750010) and 1.00 grams of SMP and 6 ml of deionized water containing Triton X-100 SigmaUltra (Sigma T9284) at 0.1% by weight. The solution was mixed for 10 minutes at 35-40 C, and then 1.3 grams of corn starch, Argo 100% food grade, was added to the solution and mixed with good agitation at 35-40 C for additional 15 minutes. The high viscosity solution/slurry was then cast on Reynolds Wrap Release Non-Stick Aluminum Foil. A blade was used to spread the materials uniformly and then dried on an oven at 85-95 C for 30 minutes. The sample was then further reacted at 160 C for 6 minutes in press oven. After removing and cooling, the sample was peeled off from the release aluminum sheet. The resulting product was in the form of a semitransparent film. (It could be used as is.) We placed the product in 400 ml of deionized water and allowed it to swell into the slurry which was allowed to settle; then it was washed with two additional 400 ml of deionized water and filtered and dried at room temperature to a fine powder. (One can use Teflon coated aluminum film instead of Reynolds Wrap with equal result.)

Comparative Example 3

In this example phosphorylation of the starch was carried out as in Example 3 above but without the conjugating reagent, urea. A solution of phosphorylation reagent was made by dissolving 1.00 grams of SMP and 6 ml of deionized water containing Triton X-100 SigmaUltra (Sigma T9284) at 0.1% by weight. The solution was mixed for 10 minutes at 35-40 C, and then 1.3 grams of corn starch, Argo 100% food grade, was added to the solution and mixed with good agitation at 35-40 C for additional 15 minutes. We did not observe any viscosity built up during this step. The slurry was then cast on Reynolds Wrap Release Non-Stick Aluminum Foil. A blade was used to spread the materials uniformly and then dried on an oven at 85-95 C for 30 minutes. The sample was then further reacted at 160 C for 6 minutes by placing in oven. After cooling, the sample was removed from the release aluminum sheet. The resulting product was in the form of a powder. We placed the product in 400 ml of deionized water and mixed and then it was allowed to settle; then it was washed with two additional 400 ml of deionized water and filtered and dried at room temperature to a fine powder.

The above Examples and Comparative Examples were then studied according to the following methodology.

a. Elastase. The concentration of the elastase in the original solution and the solution after the incubation was measured by reacting with N-methoxysuccinyl-ala-ala-val p-nitroanilide substrate using a 96-well spectrometer (Bio-TEK, Microplate Reader; Model Power Wave HT) operating at 550 nm. Known amounts of elastase were used to generate standard curves.

b. Collagenase. The activity of collagenases was monitored utilizing assay kit form Molecular Probe (EnzCheck E-12055). This assay allows accurate analysis of the metalloproteinases and their inhibitors in a rapid and high throughput format. The enzyme kit contains a gelatin fluorescent conjugate. The substrate is efficiently digested by gelatinases and collagenases to produce highly fluorescent peptides. The increase in fluorescence is proportional to proteolytic activity and will be monitored with a fluorescence micro plate reader. The assay was run on a Bio-Teck Multi-Detection Microplate Reader, Model FLx800 at 485 nm excitation and 530 nm detection.

c. Synthetic Wound Fluid. Synthetic wound fluid was made up by dissolving elastase from human leukocytes (Sigma E-8140) in HEPES buffer (pH 7.5, 0.1M 4-(2-Hydroxyethyl) piperazine-1-ethane sulfonic acid [HEPES], 0.5M NaCl, Triton X-100). The solution is diluted in the same buffer to elastase concentration of 25 mu/ml. This solution was used for assessment of elastase sequestration in the experiments reported herein.

d. Wound Fluids from Chronic Wound. Wound fluid was obtained by extracting from sponges used on wounds. The fluid was squeezed from the sponges and placed in tubes for storage in the freezer. The elastase content of the wound fluid was determined by calibrating against a standard curve of elastase (Sigma E-8140). Once the elastase content of the wound fluid was determined, it was diluted to an active elastase concentration of 25 mU/ml. Dilution was done using a HEPES buffer (pH 7.5, 0.1M 4-(2-Hydroxyethyl) piperazine-1-ethane sulfonic acid [HEPES], 0.5M NaCl, Triton X-100).

Assay Procedure. The cotton samples were then cut into 50 mg pieces and each placed in a 3 ml syringe. Holding the syringe upright, 66 µl of diluted wound fluid was added to each sample. The samples were then incubated for 2 hours. The liquid was removed from the samples and 100 µl from each sample placed in a well of a 96 well-plate. 100 µl of substrate (Methoxysuccinyl-Ala-Ala-Pro-Val-paranitranilide, 0.36 mg/ml) was then placed in each well containing a sample. Kinetic reads were performed in a spectrophotometer at 405 nm. Starch samples were analyzed by the same procedure except that after incubation, the starch slurry was filtered through a 5 micrometer Millex-SV syringe and the eluent was analyzed by reacting with the substrate as described.

Protease Sequestering Efficiency. The ability of each sample product to remove proteases (elastase or collagenases) from the wound environment was measured using absorption technique. Samples of the product were incubated with a measured volume of fluid containing the protease at a concentration simulating wound fluid. After incubation the fluid was removed by mechanical means (squeezing or centrifugation) and the concentration of the unbound elastase was measured. The activity is reported as the % elastase removed from the fluid. Pressure ulcer wounds were mimicked by incorporating neutrophil elastase or collagenase into plasma. Normally between 30-100 mg of samples was incubated with 0.5 to 1.0 ml of the simulated wound fluids with incubation time of 1-3 hours.

Discussion of Experimental Results

Fluid Sorption Capability. Conventional phosphorylated starches (Comparative Examples 1, 2, 3) were found to be not much different in their ability in absorbing fluids than standard native starch. At best they take up about their weight of water leaving higher volume of fluid on the outside. However, Examples 1, 2, 3 corresponding to product according to this invention have much better fluid sorption capability as shown in FIG. 1. For instance, product from inventive Example 3 can take up more than 35 times its weight of fluid. This ability to take-up fluid is very important in controlling the wound environment and facilitating healing process while still retaining a sufficiently moist environment for proper healing.

Elastase Removing Capability for Powders. The elastase sequestering capabilities of respective product are tabulated in Table 1 below and are compared to corn starch:

TABLE 1

| Sample | % Elastase Remove |
|---|---|
| Corn Starch | 8.4 |
| Example 1 | 55.9 |
| Example 2 | 64.5 |
| Example 3 | 63.0 |
| Comparative Example 1 | 10.1 |
| Comparative Example 2 | 7.4 |
| Comparative Example 3 | −5.3 |

As can be seen from above Table 1, samples according to this invention have significantly higher elastase sequestering effect than native corn starch, and much higher than conventional phosphorylated starches (Comparative Examples 1, 2, 3). Comparative Example 3 resulted in negative data indicating that not only did the sample fail to sequester elastase, but, probably due to changes of the pH, it seems to have enhanced the elastase activity, making that sample not good for wound healing.

The above Comparative Examples 1, 2, 3 may be understood to correspond to the phosphorylated starch that Meyer '100 describes at column 6, Example 1 (that Meyer cites as being based on U.S. Pat. No. 2,884,414), based on reacting starch with monosodium phosphate (MSP) to generate a conventional phosphorylated product. Such conventional phosphorylated product has only phosphorylated groups (Starch-O—$PO_3^{31}$ H), which provide starch with a negative charge. The phosphorylation can be low or high. Normally about 10% of the OH groups are phosphorylated with conventional phosphorylating agents such as MSP. The conventional phosphorylated products fail to swell readily and only dissolve when heated to above 70° C. The phosphorylated starches of Meyers '100 may be expressed as $[-St-(O-PO_3H^-)_x(OH)_y]_n$ where "St" is $C_6H_4O_2$; x+y=3 and x is less than 1; and "n" is between 100 and 10,000 (inclusive), which is a molecule which is only partially phosphorylated starch.

By contrast, an inventive phosphorylated starch that includes a urea network provides high swellability which the conventional phosphorylated starch lacking the urea network cannot provide. For example, for inventive Examples 1, 2, 3, water is absorbed at room temperature in excess of 30 times of the weight of the inventive example; the comparative Examples 1, 2, 3 fail to provide such swelling performance. From the data, the novel starch based derivative of the inventive Examples is substantially more effective than the conventional phosphate starches in sequestering both elastase and collagenase. Based on this data, products using the inventive phosphate starch derivatives of formula (I) would be more effective for wound healing and other related applications.

Having obtained certain experimental findings for starches, the present inventors further considered whether similar advantages could be obtained when working with cotton rather than starch. While certain advantageous results in cotton were obtained, the present inventors found that in certain circumstances, cotton and starch behave differently (for example, thiourea processing of cotton was found to be significantly more beneficial compared to thiourea processing for starch; also, a urea formaldehyde condensation product was found to provide superior activity when used on cotton but not on starch), which finding was surprising.

Inventive Example 4

Directly Placing Inventive Phosphorylated Starch on Cotton Gauze

Phosphorylation solution was prepared by dissolving 10.0 grams of MAP, 30.0 grams of urea and 0.11 gram Triton X100 and about 110 ml of water. The total volume of the solution was 105 ml. To 12.2 grams of the above solution was added 1.53 gram of corn starch and the resultant mixture was mixed for 2 minutes to get a uniform slurry. To this slurry was added 2.827 gram of dry cotton gauze. The gauze was squeezed to remove some of the liquid and then allowed to absorb the liquid 3 times to get a uniform distribution of the slurry, and then it was squeezed partially to allow retainment of 5.85 grams of the starch suspension. The wet gauze was then placed on a hot plate at 75-85 C and allowed to dry for 15 minutes. It was then cured on a press oven with uniform temperature of 160 C for 3 minutes. The gauze was then washed with deionized water three times and then dried.

Figure 1A:
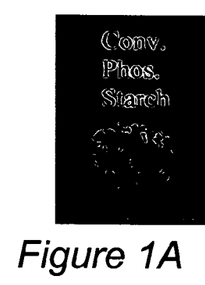
FIGS. 1A-1D are photographs showing a comparison of swelling behavior of conventional (FIGS. 1A, 1C) phosphorylated starch versus inventive starch (FIGS. 1B, 1D).
Figure 1B:
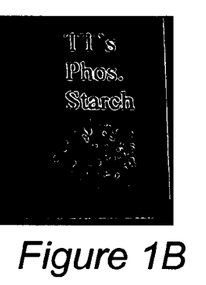
Figure 1C:
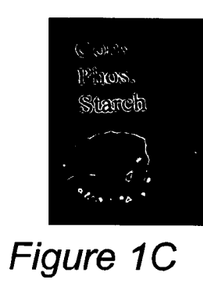
Figure 1D:
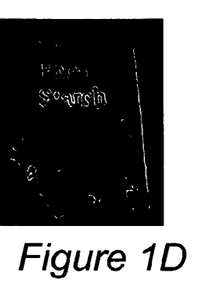
Figure 2:
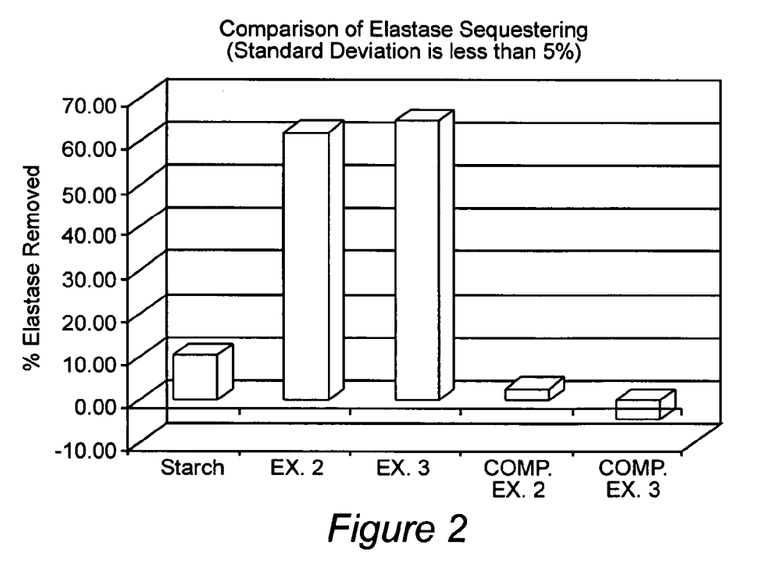
FIG. 2 is a graph comparing elastase sequesting efficiency of inventive starch derivatives against conventional phosphorylated starches and native corn starch.
Figure 3:
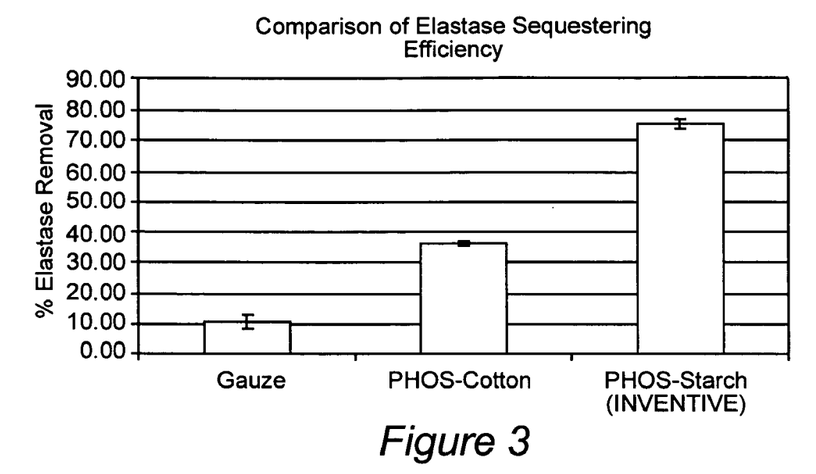
FIG. 3 is a graph comparing elastase sequestering (removing) efficiency of inventive products (PHOS-Starch) versus cotton gauze (GAUZE) and phosphorylated cotton (PHOS-Cotton).
Figure 4:
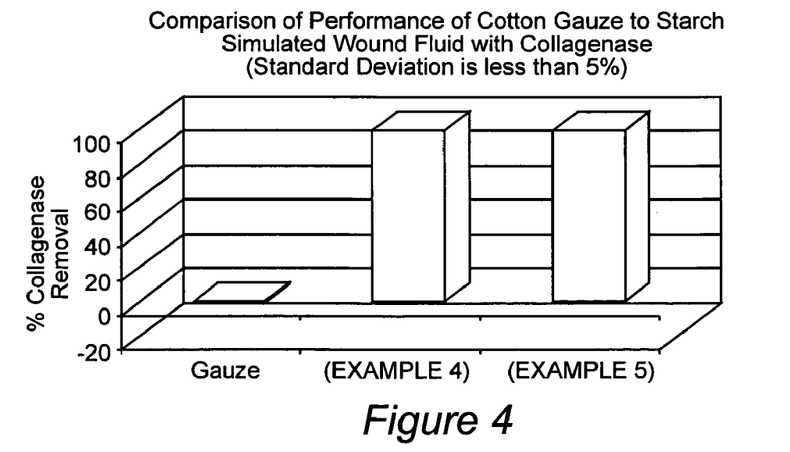
FIG. 4 is a graph comparing performance of cotton gauze to starch, using simulated wound fluid with collagenase. Standard deviation is less than 5%. Inventive cotton gauzes are compared versus standard cotton gauze.

Collagenase sequestering capacity of an inventive phosphorylated starch/cotton gauze is shown in Table 2 below and in FIG. 4.

TABLE 2

| Sample | % Collagenase Removed |
| --- | --- |
| Cotton Gauze | 0.1% |
| Example 4 | 99.3% |

As can be seen from Table 2 above, the product using inventive Example 4 removes more than 99% of the collagenase from the wound fluids and thus is characterized as superb wound healing material.

Example 4A

Phosphorylation of Cotton Gauze in the Absence of Starch

Phosphorylation solution was prepared by dissolving 10.0 grams of MAP, 30.0 grams of urea and 0.11 gram Triton X100 and about 110 ml of water. The total volume of the solution was 105 ml. To 12.2 grams of the above solution was added 2.8 gram of dry cotton gauze. The gauze was squeezed to remove some of the liquid and then allowed to absorb the liquid 3 times to get a uniform distribution of the slurry, and then it was squeezed partially to allow retainment of 5.8 gram of the starch suspension. The wet gauze was then placed on a hot plate at 75-85 C and allowed to dry for 15 minutes. It was then cured on a hot plate with uniform temperature of 160 C for 3 minutes. The gauze was then washed with deionized water three times and then dried.

Elastase removing capacity is shown in Table 3 below.

TABLE 3

| Sample | % Elastase Removal |
| --- | --- |
| Cotton Gauze | 10% |
| Example 4A Phosphorylated cotton | 35% |
| Example 4 Phosphorylated Starch on Cotton Gauze | 75% |

Product according to Example 4A is improved compared to cotton gauze in sequestering elastase. As can be seen from this data in Table 3, phosphorylation of cotton enhances the elastase removal efficiency of cotton. The elastase removal effect is substantially enhanced when starch is incorporated in the structure.

Example 5

Analogous examples to Examples 1, 2, 3 were prepared except that the starch reaction mixtures were mixed for short time (6 minutes) at 22 C before they were cast and cured in a convection oven. These samples (Examples 5A, 5B, 5C) were cured for 10 minutes at 180 C. The sample temperatures were in the range of 150-158 C during curing. The phosphorylating solution used were: 30% wt Urea, 10% MAP for Example 5A, 10% DAP for Example 5B and 10% SMP for Example 5C respectively. Referring to Table 4, lower mixing temperature and time during sample preparation resulted in products with higher efficiency for elastase sequestration. Reaction conditions have some significant effect on product elastase sequestering efficiency. For samples in which the reaction mixtures were mixed for a shorter time at a lower temperature had better elastase sequestering efficiency.

TABLE 4

| | Reaction Composition | | | % Elastase Removal |
| --- | --- | --- | --- | --- |
| | Starch Wt (g) | Phosphorylation Solution wt (g) & (Type) | Casting Conditions Time and Temp. | form Synthetic Wound Fluid |
| Ex. 5A | 5 | 38.2 (MAP) | Solution Mixed for 6 min at 24 C. then cast | 88.3 |
| Ex. 5B | 5 | 35.4 (DAP) | Solution Mixed for 6 min at 24 C. then cast | 94 |
| Ex. 5C | 5 | 36.2 (SMP) | Solution Mixed for 6 min at 24 C. then cast | 84.1 |

Example 6

Samples 6A and 6B were prepared as shown in Table 5. The elastase removal efficiency for these samples was measured using wound fluid from a patient with chronic wounds. The phosphorylation solution was made by dissolving 30 g urea, 10 g DAP and 0.1 g Triton X-100 in 60 g water. With a longer contact time (1 hour) of the starch with the reaction medium, the product had less elastase sequestering efficiency as seen in Table 5 by comparing Examples 6A and 6B).

TABLE 5

| | Reaction Composition | | | % Elastase Removal |
|---|---|---|---|---|
| | Starch Wt (g) | Phosphorylation Solution wt (g) & (Type) | Casting Conditions Time and Temp. | form Chronic Wound Fluid |
| Example 6A | 5 | 35.0 (DAP) | Solution Mixed for 6 min at 24 C. then cast | 81.4 |
| Example 6B | 5 | 29.5 (DAP) | Solution Mixed for 60 min at 24 C. then Cast | 39.0 |

Samples were cured for 7 minutes in a press oven at 160 C.
The sample temperature was in the range of 160 C. +/− 1 C. during Curing Example 7

Silver Starch Derivatives

Phosphorylated starches were treated with silver nitrate to convert them to their silver salts, to prepare silver starch derivatives of Examples 7A, 7B, 7C, 7D and 7E as shown in Table 6. The given weight of the starch was placed in a solution of silver nitrate solution and allowed to remain in contact for 10 minutes. Then the starch product was separated and washed twice with 100 ml of deionized water and dried. The comparative example was done by treating underivatized starch with silver nitrate and washed with deionized water to remove excess silver nitrate.

As the experimental data in Table 6 shows, silver derivatives of phosphorylated starch display permanent (post-washing) improvement in elastase sequestering over comparable phosphorylated starch unreacted with silver.

TABLE 6

| Example | Starch - Type | Wt of Starch Product (mg) | Deionized water (ml) | Silver nitrate solution (microliter) | % Elastase Sequestering (from a patient wound fluid) |
|---|---|---|---|---|---|
| 7A | Phosphorylated MAP/Urea | 500 | 100 | 50 | 74.4 |
| 7B | Phosphorylated MAP/Urea | 500 | 100 | 500 | 83 |
| 7C | Phosphorylated MAP/Urea | 500 | 100 | 2000 | 89.3 |
| 7D | Phosphorylated MAP/Urea | 500 | 100 | 5000 | 93.3 |
| 7E | Corn Starch | 500 | 100 | 2000 | 20.1 |

Phosphorylated starch without silver derivatization has elastase sequestering efficiency of 70%

By the optional silver derivatization of inventive starch derivatives, somewhat better elastase-sequestering results have been obtained in the examples tested.

Example 8

Other co-reagents in place of a urea co-reagent in the phosphorylation reaction were examined for derivatization of starch, cellulose, alginates and other carbohydrates. Urea was substituted with other potential reactants given in Table 7.

Because of low solubility of some of the co-reagents we used dimethyl sulfoxide (DMSO) as a co-solvent in addition to water. A 30/10 wt ratio of the Co-reagent/MP was used. Co-reagent (0.95 g) was dissolved in 3 ml of DMSO, and 1.6 ml of water. In case of cyanuric acid an additional 2 ml of DMSO was needed, to obtain a solution. The phosphorylation reagent (0.32 g MAP) was dissolved in 3 ml of water. Then the two solutions were combined to form the reagent solution. We soaked 2 g of the cotton gauze in the solution and then squeezed out the excess solution. The wet cotton gauze was dried at 80-90 C and weighed to measure dry pick up weight of the reagent. The coated gauze was then cured at 160 C for 9 min and then washed with water to remove unbound materials.

TABLE 7

| Example | Co-reagent | Reagent | Wt of Original Cotton Gauze (g) | Wt of Dried Gauzed with Reagents (g) | % Elastase Sequestering |
|---|---|---|---|---|---|
| 165-A | Thiourea | MAP | 2.01 | 3.22 | 51.5 |
| 165-B | Biuret | MAP | 2.02 | 3.3 | 37.7 |
| 165-C | Cyanuric Acid | MAP | 2.02 | 3.28 | 28.5 |
| 165-D | Urea | MAP | 2.01 | 3.23 | 42.5 |
| | Cotton Gauze | | | | 24.8 |

As can be seen from Table 7, each of the treated samples 165-A, 165-B, 165-C and 165-D have a better elastase sequestering effect than untreated cotton. The order of activity in decreasing order is thiourea>urea>biuret>cyanuric acid.

Example 9

Phosphorylated Derivative of Alginate on Cotton

Ammonium alginate was phosphorylated with a combination of urea (30 wt %)/DAP (10 Wt %) in water and then put on a cotton fabric and cured. To 10 gram of the phosphorylation solution was added 0.5 g of ammonium alginate (Protamon S, FMC Biopolymers) and the slurry was mixed for 3 minutes. Two grams of cotton gauze was immersed in the solution and then was squeezed out to remove the excess solution. The wet fabric was then dried at 80-90 C and cured according to Table 8. The elastase sequestering of the fabric was determined after 3 washes with Deionized water.

TABLE 8

| | Cured Time (Min) | Cure Temperature (160 C.) | Elastase % Sequestered |
|---|---|---|---|
| 142-1A | 6 | 160 | 38.7 |
| 142-1B | 10 | 160 | 35.2 |
| Cotton Gauze | | | 11.6 |

Example 10

Silver Treated Phosphorylated Cotton

The phosphorylated gauze (Examples 10a, 10b) used in this experiment was made with 30/16 urea/DAP under mild reaction conditions (cure time about 10 min and cure temperature range of 130-145 C). Examples 10a, 10b, 10c and 10d were made according to Table 9 by contact of the fabric with dilute solutions of silver nitrate. A given quantity of phosphorylated gauze was permitted to equilibrate with a volume of soluble silver nitrate solution. The contact time was 3 minutes. The fabric after equilibration was washed 3 times with a large volume of water (300 ml) under high agitation at room temperature. For comparison the same treatment was done with untreated cotton gauze under ideal conditions and the elastase sequestering efficiency was measured (Table 9).

The present inventors have discovered that their inventive phosphorylated products have unexpectedly superior performance when treated with silver solutions. These products have exceptional performance in elastase sequestering, great washfastness (permanency), and also release silver only slowly meaning that they will have superior antimicrobial activity.

TABLE 9

| | Silver Treating Conditions | | | % Elastase Sequestered | | |
|---|---|---|---|---|---|---|
| Base Gauze | Wt of Gauze (g) | Microliter of AgNO3 Solution | ml Di H2O | Original Before Silver Derivative | Silver Treated Before Wash | Silver Treated After Wash |
| Ex. 10a Phosphorylated Cotton Gauze | 1.0 | 2000 | 25 | 40 | 94 | 94 |
| Ex. 10b Phosphorylated Cotton Gauze | 1.0 | 500 | 25 | 40 | 81 | 71 |
| Ex. 10c Cotton Gauze | 1.0 | 2000 | 25 | 21 | 43 | 34 |
| Ex. 10d Cotton Gauze | 1.0 | 500 | 25 | 21 | 35 | 27 |

As Table 9 shows, the sequestering efficiency changes from 40% in the phosphorylated cotton to 81% and 94% in the silver derivatives and does not change after severe wash with water, which indicates that the silver derivative product has stable structure and does not loose silver upon wash. The cotton gauze shows an opposite result, by showing some improvement on sequestering performance, but upon wash the gain in sequestering is significantly lost.

Example 11

Examples Z1-Z8 were various phosphorylated cotton gauze made, by varying the ratio of the phosphorylating agent (30 wt Urea/16 wt MAP) to cotton gauze to achieve uncured gauzes with different % solid to cotton. These materials were then cured for 9 min at 150 C under press oven and then converted into silver derivative by equilibrating 0.5 g of the fabric with 10 ml of 0.135 mg/ml silver nitrate solution for ten minutes after which the treated fabrics were then washed twice with 80 ml of deionized water for 5 minutes each time and then dried and tested for elastase sequestration.

TABLE 10

| | | Phosphorylated Gauze | |
|---|---|---|---|
| | % Solid | Before Silver Treatment % Elastase Sequestered | After Silver treatment |
| Example Z1 | 40.4 | 52.1 | 93.6 |
| Example Z2 | 38.3 | 56.7 | 95.3 |
| Example Z3 | 31.5 | 52.5 | 95.6 |
| Example Z4 | 25.4 | 68 | 96.3 |
| Example Z5 | 23.3 | 62.5 | 96 |
| Example Z6 | 20.3 | 69 | 93 |
| Example Z7 | 20.1 | 65.4 | 95.8 |
| Example Z8 | 13.3 | 54.2 | 96.3 |

% solid is Wt % MAP and Urea on uncured sample

As the data in Table 10 show, silver derivatization according to the present invention, to produce silver-derivatized phosphorylated gauze, substantially improves elastase sequestering compared to phosphorylated gauze.

Example 12

Three sulfonated polymers (poly(sodium 4-styrene-sulfonate; poly(anetholesulfonic acid sodium salt; and poly(vinyl sulfate, potassium salt) were respectively prepared as comparative examples according to Table 11 below. We coated cotton fabrics with 1% of the sulfonated polymers described in Table 10, and then equilibrated them with a solution of silver nitrate. We used 50 mg of each sample and placed it in 15 ml of aqueous silver nitrate solution (0.13 mg/ml) for 7 minutes. Then the samples were washed twice with 50 ml deionized water and then dried. These three sulfonated polymers are considered the base samples.

As the inventive sample for the comparison, a phosphorylated cotton was prepared with urea/DAP.

TABLE 11

| | Elastase Sequestering | | |
|---|---|---|---|
| | Before Silver Treatment | After Silver Treatment | Change % due to Silver |
| Poly(sodium 4-styrene-sulfonate) AId 243051 | 70.6 | 72.5 | 2.7 |
| Poly(anetholesulfonic acid sodium Salt) AId 10820HA | 71.7 | 72.7 | 1.4 |
| Poly (vinyl sulfate, potassium Salt) AId 08316HC | 69.8 | 76.7 | 9.9 |
| (INVENTIVE) Phosphorylated cotton Urea/DAP | 50.1 | 93.3 | 86.2 |

Referring to Table 11, the inventive phosphorylated cotton compared to the coated cotton fabric showed significantly better performance. The inventive silver treated phosphorylated cotton sample had a durable elastase sequestering capability, and also retained silver through washing meaning that it will have good antimicrobial properties.

Example 13

Water Uptake

Sample V1 was prepared by phosphorylating starch with a solution composition of 30 Urea/10 MAP. Sample V2 was prepared by phosphorylating starch with a solution composition of 3 Urea/10 SMP.

Sample V3 was prepared by reacting 5.0 gram starch by mixing with a solution of 7.5 g urea in 15 ml of water for 1.5 minutes before it was cast on silicone coated aluminum foil and dried at 85-90 C. It was then cured at 160 C for 7 minutes followed by washing with deionized water (3 times with 600 ml of water) and dried at room temperature.

Water uptake was measured by placing 0.30 g of each derivative in a plastic boat (10 gram capacity). Deionized water was poured into each boat to wet the sample and then enough water was added to totally soak the sample. Additional water was then added the sample was allowed to equilibrate. The excess water was then removed by bringing the excessively wetted samples in contact with paper towels allowing removal of free water by capillary action for 3 minutes. The weight of absorbed water was measured by weighing. The water uptake is given in g of water taken per gram of sample. It is apparent from this experiment (Table 12) that inventive starch samples have extremely high capacity for aqueous uptake. Interestingly a sample of starch reacted with only urea has higher water uptake than conventional phosphorylated sample, but neither shows water uptake capacity as much as the inventive samples.

TABLE 12

Water Uptake by Starch Derivatives

| Example # | Description of Sample | % Elastase removed, Synthetic WF | Water Uptake (g water/g Starch Derivative) |
|---|---|---|---|
| V1 | Phosphorylated with 30Urea/10 MAP | 85 | 41 |
| V2 | Phosphorylated with 30Urea/10 SMP | 86 | 28 |
| V3 | Reacted with only Urea Solution | 10 | 2 |
| Comparative Example 3 | Phosphorylated with SMP Only | −6 | 0.5 |

From Table 12, it is apparent that water uptake as well as elastase sequestration is strongly dependent on the presence of phosphorylating agent as well as the conjugating reagent (urea). High degree of water uptake is an advantageous property for a wound care product, and thus the inventive samples (such as Examples V1, V2) are advantageously used as wound care products.

Example 14

Preparation of Starch/Urea Products with Anionic Derivatizing Agents

Table 12 demonstrates that phosphorylating reagent enhances the sequestering ability of the starch product. In addition as shown in Table 12 the phosphorylating reagent increases the water uptake capacity dramatically. For a description of mechanism of the reaction, see "Some studies on starch-urea-acid reaction mechanism", Carbohydrate Polymers 48 (2002) 255-261. The present inventors evaluated other anionic derivative reagents with urea/starch reaction to see whether other acids or acid salts provide product with appropriate protease sequestering and water uptake. Table 13 below shows performance of some of these derivatives. Although most of these starch/urea derivatives have respectable elastase sequestering capacity, their water uptake and swelling behavior is not as good. Contrary to samples Z1 and Z2 which have a water uptake of 2-3 (g water/g sample), sample Z3 is almost soluble leaving small amount of insoluble. None of these non-phosphorylated starch/urea products were highly swellable like the inventive phosphorylated/Starch Urea products which have water uptake of <10 and most preferably <20.

TABLE 13

Starch/Urea Derivatives with other Acid Salts

| Experiment No. | Salt | Elastase Sequestering, Synthetic WF | Water Uptake g/g |
|---|---|---|---|
| 189A | Z1 Ammonium Sulfate | 55.9 | 2.80 |
| 189B | Z2 Ammonium Chloride | 51.6 | 1.97 |
| 189C | Z3 Sodium Bisulfite | 58.0 | Partial Soluble* |

*the sample is mostly soluble
Composition of Solution: 30 g Urea/10 g Salt/60 g water
Starch Reaction Composition: 2.5 g Starch and 6.5 g solution

Example 15

New Cotton Derivatives with Exceptional Protease Sequestering Capacity

The present inventors have discovered a new series of condensation products of inventive sequestering reagents such as urea and thiourea with formaldehyde producing networks of outstanding capacity with or without the phosphorylation reagents. Products formed from these reagents with cotton give outstanding performance in protease sequestration.

The reaction product with starch produces some elastase sequestering, but the performance of phosphorylated/urea starch products in respect to elastase sequestrations and water uptake is superior.

The cotton derivatives of this Example 15 were made following the procedure described by Khalil et al, "Preparation of some starch based neutral chelating agents," Carbohydrate Research 324, (2002) 189-199.

Preparation of Methylol Derivatives: Methylol derivatives of urea and thiourea were prepared by reacting the nitrogen containing derivatives with formaldehyde using the molar ratios of 1:1.1 and 1:2.1 respectively. The pH of the solution was adjusted to 9.0 using triethanolamine (TEA) and the reaction mixture was kept at room temperature for 24 hours. For example when preparing urea/formaldehyde 1:1.1 condensation product dissolved 66.0 grams urea was dissolved in 90.4 g 37% formaldehyde; after adjusting pH to 9.0 by addition of TEA the preparation was allowed to sit for 24 hours at room temperature.

Preparation of Condensation Product with Phosphorylating Agent. The phosphorylated analogue was prepared by dissolving DAP in minimal volume of water and the resulting solution was added to the condensation product at a ratio of 0.16 g DAP solid/1.0 g of the condensation product. For example 1.62 g of DAP was dissolved in 2.7 g deionized water and then the solution was added to 10 gram of the 1:1.1 urea/formaldehyde solution.

Cotton Derivatives of the Condensation Products. 4.0 gram of the product was mixed with 0.4 g magnesium chloride (catalyst), then 2.0 gram cotton gauze was soaked in the solution, followed by squeezing out to get 1.4-1.6 wet pick up (wt of wet resin/g dry cotton). The wet cotton was then dried at 80-90 C and then cured for 10 or 20 minutes at 150 C. The cured cotton was washed (3×400 ml water) to remove the soluble fraction and dried at 90 C. When phosphorylated analogue was used, no magnesium chloride catalyst was used.

Starch Derivatives of the Condensation Products. 2.0 g starch was mixed with 2.0 g condensation product, 0.2 magnesium chloride for 3 minutes and then cast on aluminum foil and allowed to dry at 80-90 C. The solid was cured at 150 C for 20 minutes. It was broken up and washed with 3×100 ml of deionized water and then dried.

Sample Designation: Samples are designated by giving condensation type, conjugating reagent type (U for urea, TU for thiourea) followed by phosphorylation reagents (DAP for example). Thus 1:1.1-(U/F) represents 1:1.1 urea/formaldehyde resin without phosphorylation agent; 1:2.1 (TU/F) represents 1:2.1 thiourea/formaldehyde without phosphorylation agent; 1:1.1 (U/F) (DAP) represents 1:1.1 urea/formaldehyde resin with DAP as phosphorylating agent.

TABLE 14

Performance of Cotton Derivatives of the Condensation Products

| Example No. | Sample Designation | Cure time Min | % Elastase removed, Synthetic WF |
|---|---|---|---|
| W-1 | 1:1.1 U/F | 20 | 83 |
| W-2 | 1:2.1 U/F | 20 | 42 |
| W-3 | 1:1.1 U/F DAP | 10 | 57 |
| W-4 | 1:1.1 TU/F | 10 | 81 |
| W-5 | 1:2.1 TU/F | 10 | 99 |
| W-6 | 1:1.1 TU/F DAP | 20 | 99 |

As can be seen, most of these cotton derivatives in Table 14 with and without phosphorylating agents are powerful protease sequesterants.

TABLE 15

Performance of Starch Derivatives of the Condensation Products

| Example No. | Sample Designation | Cure time Min | % Elastase Removed, Synthetic WF |
|---|---|---|---|
| Y-1 | 1:1.1 U/F | 20 | 18 |
| Y-2 | 1:2.1 U/F | 20 | 12 |
| Y-3 | 1:1.1 TU/F | 10 | 42 |
| Y-4 | 1:2.1 TU/F | 10 | 18 |
| Y-5 | 1:1.1 U/F DAP | 10 | 23 |
| Y-6 | 1:1.1 TU/F DAP | 10 | 41 |

Starch derivatives Y-3 and Y-6 in Table 15 are better in elastase-sequestering performance than underivatized starch. For most starch unphosphorylated derivatives in Table 15, better elastase removal performance would be obtained from a corresponding product with phosphorylation of starch in the presence of urea.

While the invention has been described in terms of its preferred embodiments, those skilled in the art will recognize that the invention can be practiced with modification within the spirit and scope of the appended claims.

What we claim as our invention is:

1. A cotton gauze, comprising silver-derivatized phosphorylated cotton gauze.

2. The cotton gauze of claim 1, having great washfastness.

3. The cotton gauze of claim 1, wherein the product releases silver only slowly.

4. The cotton gauze of claim 1, wherein elastase sequestering activity survives washing.

5. The cotton gauze of claim 1, having elastase sequestering activity of about 81% or higher, said elastase sequestering activity surviving wash of the product without losing more than 10% sequestering activity.

6. The cotton gauze of claim 1, having elastase sequestering activity of about 94%, said elastase sequestering activity surviving wash of the product.

7. The cotton gauze of claim 1, having a color other than black provided that the product avoids contact with intensive ultraviolet light.

* * * * *